United States Patent [19]

Higashi et al.

[11] Patent Number: 4,933,182
[45] Date of Patent: Jun. 12, 1990

[54] PHARMACEUTICAL COMPOSITION FOR TREATING PERIODONTAL

[75] Inventors: Kiyotsugu Higashi, Nara; Shigeru Kametaka; Reiko Izumi, both of Osaka; Katsuhiko Morisaki, Nara; Shin'ichi Hayashi, Osaka, all of Japan

[73] Assignee: Rohto Pharmaceutical Co. Ltd., Osaka, Japan

[21] Appl. No.: 414,602

[22] Filed: Sep. 29, 1989

Related U.S. Application Data

[63] Continuation of Ser. No. 29,658, Mar. 24, 1987, abandoned.

[30] Foreign Application Priority Data

Mar. 25, 1986 [JP] Japan ................................. 61-67810

[51] Int. Cl.$^5$ ..................... A61L 15/03; A61K 9/70; A61K 31/78; A61F 13/00
[52] U.S. Cl. ..................................... 424/435; 424/78; 424/81; 514/900; 514/902
[58] Field of Search ........................... 424/78, 81, 435; 519/900, 902

[56] References Cited

U.S. PATENT DOCUMENTS

| | | | |
|---|---|---|---|
| Re. 33,093 | 10/1989 | Schiraldi | 424/449 |
| 3,909,444 | 9/1975 | Anderson | 252/316 |
| 4,370,136 | 1/1983 | Widman | 433/217.1 |
| 4,426,373 | 1/1984 | Morton et al. | 424/52 |
| 4,482,535 | 11/1984 | Sugar et al. | 424/81 |
| 4,537,765 | 8/1985 | Gaffar et al. | 424/53 |
| 4,550,018 | 10/1985 | Ambike et al. | 424/52 |
| 4,568,535 | 2/1986 | Loesche | 514/365 |
| 4,569,837 | 2/1986 | Suzuki et al. | 514/902 |
| 4,661,341 | 4/1987 | Benedict et al. | 424/81 |
| 4,663,152 | 5/1987 | Barth et al. | 424/7.1 |
| 4,681,544 | 7/1987 | Anthony | 433/215 |
| 4,701,320 | 10/1987 | Hasegawa et al. | 514/900 |
| 4,702,905 | 10/1987 | Mitchell et al. | 424/49 |
| 4,713,243 | 12/1987 | Schiraldi et al. | 424/435 |
| 4,740,365 | 4/1988 | Yukimatsu et al. | 424/435 |
| 4,764,377 | 8/1988 | Goodson | 424/435 |
| 4,772,470 | 9/1988 | Inoue et al. | 424/435 |
| 4,780,320 | 10/1988 | Baker | 424/493 |
| 4,842,846 | 7/1989 | Nakano | 514/902 |
| 4,846,165 | 7/1989 | Hare | 424/435 |
| 4,892,736 | 1/1990 | Goodson | 424/435 |

FOREIGN PATENT DOCUMENTS

| | | |
|---|---|---|
| 0135022 | 3/1985 | European Pat. Off. . |
| 0184389 | 6/1986 | European Pat. Off. . |
| 2109237 | 6/1983 | United Kingdom . |
| 2177708 | 1/1987 | United Kingdom . |

*Primary Examiner*—Shep K. Rose
*Attorney, Agent, or Firm*—Venable, Baetjer, Howard & Civiletti

[57] ABSTRACT

A pharmaceutical composition for treating periodontal diseases which comprises one or more of therapeutically active ingredients dispersed in a carrier, characterized in that said carrier consists of (A) water soluble polymer, and
(B) polymeric particles having a limited solubility in water, said particles being dispersed in said water soluble polymer.

4 Claims, 1 Drawing Sheet

PHARMACEUTICAL COMPOSITION FOR TREATING PERIODONTAL

RELATED APPLICATION

This is a continuation of U.S. patent application Ser. No. 029,658, filed Mar. 24, 1987, now abandoned.

This invention relates to a pharmaceutical composition which is applied to a periodontal pocket or paradentium for the purpose of treating periodontal diseases. The pharmaceutical composition, which is provided in the form of gel, sheet, film or bar-like formulation, releases a controlled and effective amount of an active ingredient at the periodontal pocket or paradentium.

The "periodontal diseases" is a general term of various inflammatory diseases of paradentium. The diseases include a series of diseases exhibiting various syndromes which vary from each other according to the stage or situation of the diseases or the age of the patient, and have not been definitely subclassified. Since, however, the term "periodontal diseases" is given to any inflammatory disease which initially occurs at a marginal gingiva area and finally reaches an alveolar bone, the diseases can be roughly divided, on the basis of the degree of the inflammation, into "gingivitis" in which the inflammation is limited to the gingiva tissue, and "paradentitis" in which the inflammation is chronic and found even in an alveolar bone. However, peculiar diseases such as "juvenilie paradentitis" and "acute necrotizing ulcerative gingivitis" are also included in the periodontal diseases.

The paradentitis, which was once called "alveolar pyorrhea", is characterized by remarkable symptoms such as inflammation of gingiva, formation of periodontal pockets, bleeding and pus discharge from said periodontal pockets, and it brings about resorption of alveolar bone, loose tooth, and shedding of tooth.

The consensus of most investigators is that the periodontal diseases is caused by bacteria present in dental plaques formed in periodontal pockets. Efforts have been concentrated on the discovery of pathogenic bacteria responsible for said diseases. At the present time, an attributable major pathogen is recognized to be a certain nigral pigment-producing bacteria, such as genus Bacteroides. However, other genus of bacteria including Actinobacillus, Capnocytophaga, Fusobacterium and Spirochetes may be included in the causative pathogens. In any case, it is an established theory that the periodontal diseases should not be attributed to all bacteria present in the dental plaque.

The periodontal diseases have previously been treated by several ways, such as exhaustive scaling of plaques in periodontal pockets, root plainning, gingivectomy to eliminate the periodontal pocket, or surgical curettage to excise inflammatory tissues. These treatments have been effective to some extent but not satisfactory.

On the other hand, pharmacotherapy has also been conducted using a drug selected from germicides, anti-inflammatory agents, plaque solubilizing agents, hemostyptics, and the like. These drugs are used in the form of the formulation suited for internal use or massotherapy (e.g., dentifrices, ointments, and the like). However, they are not satisfactory for the purpose of treatment of periodontal diseases because the internal use hardly permits the selective migration of the drug to the lesional region, and the massotherapy is not successful in solubilizing the plaques which are present beneath the gingival margin.

Recently, strips which comprise polymers and active ingredients for treatment of periodontal diseases have been developed. These strips are said useful for the treatment of plaques and inflammation beneath the gingival margin. The strips can be applied directly to the lesional region to be treated, and therefore, the active ingredient can be concentrated to the desired site selectively. This modified therapeutic method has been proved to be more effective than any conventional pharmacotherapy. For instance, J. M. Goodson et al. disclose the implantation of "hollow fiber", which contains germicides, into the gingival region (J. Clinical Periodontology, 1979: 6: 83–92). M. Addy et al. have reported the insertion of strips, which were prepared from a mixture of an insoluble polymer such as polyethylmethacrylate and germicides, into periodontal pockets (J. Periodontal, 693, Nov. 1982). In addition, insertion of the strips, prepared from a mixture of a soluble polymer and a drug, into the lesional region, such as periodontal pockets, is also reported (Japan Patent Publication No. 59-222406).

The formulations mentioned above comprise a mixture of an active ingredient and a homogeneous polymer base. Accordingly, where such formulation is designed to contain two or more active ingredients which differ from each other in terms of pharmacological activity and therapeutically effective dose, it has been impossible to prepare the formulation in which each of the plural ingredients may release independently and provide its suitable concentration as desired.

The use of the hollow fiber or insoluble polymer, as a base, causes irritation or pain to patients, and moreover, it necessitates the removal of the base after release of an active ingredient, which is often annoying. On the other hand, the strip which comprises a soluble polymer as a base or carrier permits a rapid release of an active ingredient. Accordingly, it does not afford a constant therapeutical effect and, therefore, has a poor practical use.

As the result of an extensive study for seeking a novel therapeutic composition for periodontal diseases, which suitably controls the release of one or more of active ingredients and which does not give any uncomfortable feelings to patients, it has been found that the use of a two-phase carrier base, which consists of particles comprising a polymer having a limited solubility in water and a water soluble polymer used for dispersing such particles, meets the requirements just mentioned above.

Thus, the present invention provides a pharmaceutical composition for treating periodontal diseases, which comprises one or more of therapeutically active ingredients dispersed in a carrier, characterized in that said carrier consists of (A) water soluble polymer, and (B) polymeric particles having a limited solubility, said particles being dispersed in said water soluble polymer.

Figure 1:
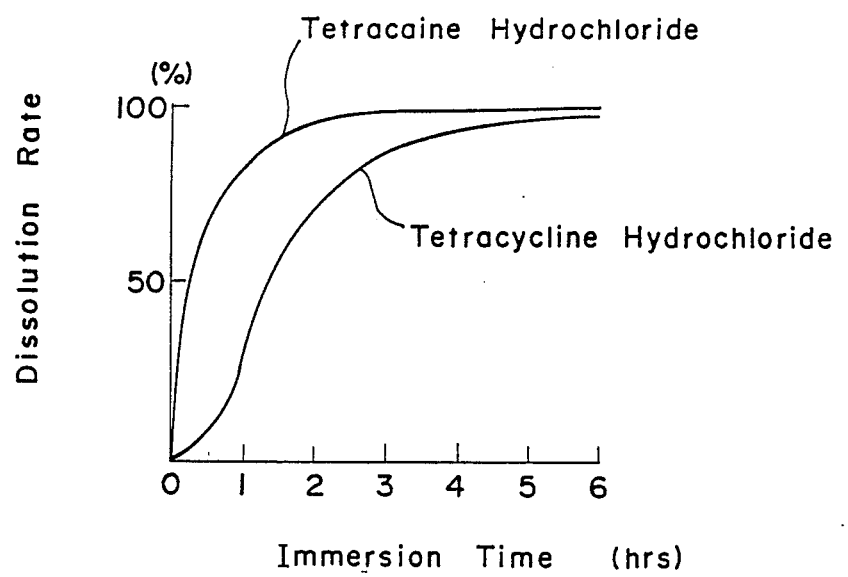
FIG. 1 shows the dissolution profile of two active ingredients contained in the pharmaceutical composition of the invention which is in the form of a film.

The term "a polymer having a limited solubility in water" herein used includes an insoluble polymer, a sparingly soluble polymer, and a polymer which dissolves in an aqueous medium within a limited pH range.

For the purpose of the present invention, the term "insoluble polymer" means a polymer which dissolves in an aqueous medium, particularly in water, in a concentration of less than 0.1% by weight, irrespective of pH.

"Water soluble polymer" or "soluble polymer" denotes any polymer which dissolves in an aqueous medium, particularly in water, in a concentration of more than 1% by weight, irrespective of pH. "Sparingly soluble polymer" means a polymer which has a solubility between the soluble polymer and the insoluble polymer or decomposes to dissolve in vivo slowly. The term "polymer which dissolves in an aqueous medium within a limited pH range" means a polymer which dissolves in an aqueous medium, particularly in water, having a pH higher than 4 or lower than 6, in a concentration of more than 1% by weight.

For the purpose of simplicity, the insoluble polymer, sparingly soluble polymer and the polymer which dissolves in an aqueous medium within a limited pH range are hereinafter referred to as "non-soluble polymer" as a whole.

The soluble polymer used in the present invention must be fabricated into a semi-solid or a solid material. The non-soluble polymer should have a property suitable for being fabricated into particles. Both soluble and nonsoluble polymers employed in the present application should be, of course, physiologically acceptable.

Specific examples of the insoluble polymer are ethyl cellulose, cellulose acetate, ethyl methacrylate / trimethylammonioethyl methacrylate chloride copolymer, and the like. The sparingly soluble polymer includes, for instance, biodegradable polymer such as polyglycolic aicd, polylactic acid, polytetramethylglycolide, polydiethylglycolide, poly- -caprolactone, poly(DL-decalactone), poly(alkyleneadipate), copolymers thereof, and ion exchange resins.

The polymer which dissolves in an aqueous medium having a pH above 4 includes copolymers consisting of acrylic acid, methacrylic acid and/or esters thereof, such as methyl acrylate / methacrylic acid copolymer, methyl acrylate / methacrylic acid / octyl acrylate copolvmer, ethyl acrylate / methacrylic acid copolymer, methyl acrylate / methacrylic acid / methyl methacrylate copolymer, and methyl methacrylate / methacrylic acid copolymer, hemiesters of organic bivalent acid with polysaccharide acetates such as cellulose acetate phthalate, cellulose acetate succinate, cellulose acetate maleate, starch acetate phthalate, and amylose acetate phthalate, hemiesters of organic bivalent acid with alkylated polysaccharides such as methyl cellulose phthalate, hemiesters of organic bivalent acid with hydroxypropylmethyl cellulose phthalate, and hydroxyethyl ethyl cellulose phthalate, hydroxypropylmethyl cellulose acetate succinate, alkyl ethers of carboxyalkylated polysaccharide such as carboxymethylethyl cellulose, hemiesters of organic bivalent acid with polyvinyl alcohol and its derivatives such as polyvinyl alcohol phthalate, polyvinyl acetate phthalate, polyvinyl acetal phthalate, and polyvinyl butylate phthalate.

The polymer which dissolves in an aqueous medium having a pH below 6 includes dimethylaminoethyl methacrylate methyl methacrylate copolymer, polyvinylacetal / dimethylamino acetate, cellulose acetate dibutylhydroxypropyl ether, and the like.

Specific examples of the soluble polymer are, for instance, methyl cellulose, hydroxypropyl cellulose, sodium carboxymethylcellulose, hydroxypropylmethyl cellulose, hydroxyethyl cellulose, sodium alginate, propylene glycol alginate, pulluran, tragacanth, xanthan gum, chitosan, polyethylene oxide, polyvinyl pyrrolidone, polyvinyl alcohol, polyacrylic acid, polymethacrylic acid, and a salt thereof.

The pharmaceutical composition of the present invention may be prepared by dispersing one or more of active ingredients into a non-soluble polymer, or both of a soluble polymer and a non-soluble polymer, and mixing these polymers, and finally forming the resultant mixture into a solid material of a film, sheet or bar-like shape, or into a semi-solid material such as gel or ointment.

In more detail, one or more of non-soluble polymers is dissolved, as the first step, in an appropriate organic solvent. To the resultant solution is dissolved or dispersed one or more of active ingredients, and the mixture is formed into film or sheet by casting method. The resultant solid material is ground into particles.

The particles are also obtainable by spray drying, Wuster coating, Coacervation, or Drying in liquid phase. The average particle size may range from $1\mu$ to $500\mu$ depending on the contemplated release pattern of the active ingredient. However, the size between $1\mu$ and $303\mu$ is generally preferred.

On the other hand, one or more of water soluble polymers are dissolved in a suitable solvent. The solvent may contain, if desired, one or more of active ingredients. Subsequently, the pH of the mixture is adjusted, if necessary, and the particles obtained above are uniformly suspended in the mixture. The pharmaceutical composition of the invention in the form of gel is thus obtained.

The composition of the invention in the form of film or sheet is obtained by deaerating the just mentioned gel, and subjecting the same to the casting process. The film or sheet may also be prepared by compression molding, extrusion or calendering. The most suitable forming process among others is selected depending on the physico-chemical properties of the polymers employed.

The bar-like composition of the invention is prepared in the similar manner as the film or sheet, but through extrusion.

The weight ratio of the particles to the soluble polymer may range from 1:99 to 99:1 on the basis of dry weight. The composition of the particles: soluble polymer in a ratio of 10:90–70:30 is preferred.

Therapeutically active ingredient or ingredients used for the preparation of the composition of the invention are selected from those effective for prevention or treatment of periodontal diseases, for example, germicides, such as chlorhexidine, Ag protein, glyceryl iodide, phenol, benzalkonium chloride, cetylpyridinium chloride, and the like; antimicrobial agents, such as ampicillin, tetracycline, benzylpenicillin, clindamycin, cefalexin, erythromycin, chloramphenicol, fragiomycin sulfate, and the like; anti-inflammatory agents, such as ibuprofen, indomethacin, ketoprofen, mefenamic acid, antipyrine, pranoprofen, ibufenac, tiaramide hydrochloride, prednisolon, dexamethasone, triamcinolone acetonide, prostaglandine, and the like; plaque solubilizing agents, such as dextranase, protease, amylase and the like; collagenase inhibitors obtained from the extraction of crude drugs, such as gambir-catechu known in the name of "asenyaku"; local anesthetics, such as tetracaine hydrochloride, ethyl aminobenzoate, and the like; antihistaminic agents, such as chlorphenilamine maleate, diphenhydramine, and the like; hemostatic agents such as tranexamic acid, and the like.

The solid composition of the invention in the form of film, sheet or bar can be prepared in different sizes. However, the convenient size of the film or sheet may be 0.1–0.5 mm in thickness, 0.5–3 mm in width, and 10–50 mm in length. The size of the bar may generally range from 0.5 to 1.5 mm in diameter and from 10 to 50 mm in length. Furthermore, the composition of the invention may be cut in suitable size by the user depending on several factors, such as severity of the disease, and the width and depth of the locus to be applied. The composition of the invention can be applied to the periodontal pocket or paradentium by insertion, injection, or rubbing according to the type of formulation.

The pharmaceutical composition of the invention exhibits a desirably controlled release pattern of the active ingredient(s). Such controlled release is attained by careful selection of a particular condition with respect to the following variables.

(1) Distribution ratio of an active ingredient between the particles and the soluble polymer.
(2) The particle size to be dispersed in the soluble polymer.
(3) Selection of non-soluble polymer or polymers which permits the modification of both the solubility of particles and diffusion velocity of an active ingredient in the particles in the manner as desired.
(4) The use of one or more kind(s) of particles which differ from each other in their solubilities.
(5) The ratio of the amounts of particles and soluble polymer to be combined.
(6) Selection of soluble polymer or polymers having desired viscosity.

By selection of suitable conditions in regard to the above variables, there is obtained the pharmaceutical composition of the invention which releases one or more of active ingredients in the manner as contemplated. Since the surface of the composition of the invention is mainly composed of water soluble polymer, it does not give any uncomfortable feeling to patients.

The following examples are presented by way of illustration of specific embodiments of the pharmaceutical composition of the invention. In examples, part or parts are represented by weight basis.

EXAMPLE 1

Poly(lactic acid) (10 parts) and tetracycline hydrochloride (2 parts) are dissolved in methylene chloride (100 parts). Flow casting of the resultant mixture yields a sheet, which is ground into particles having an average size of 50µ.

The particles (10 parts) and hydroxypropyl cellulose (10 parts) are uniformly admixed. The mixture is blended with water, extruded with pressure, and dried. The bar-like shaped product of 1.0 mm diameter is thus obtained.

EXAMPLE 2

Methacrylic acid / methyl methacrylate copolymer (1:2 molar ratio) (80 parts) is dissolved in ethanol (1000 parts). In the solution are suspended or dissolved indomethacin (5 parts) and triacetin (20 parts) and the mixture is casted into a sheet, which is then pulverized into particles having an average size of 80µ.

Hydroxypropyl cellulose (10 parts) is dissolved in water (1000 parts), and tetracycline (25 parts) is added to the resultant solution, after adjusting to pH 6.0 by addition of hydrochloric acid. The resultant mixture (80 parts) are uniformly admixed with the particles obtained above (20 parts) to yield the product in a gel form.

EXAMPLE 3

The particles produced in Example 2 (20 parts), methyl cellulose (80 parts) and tetracycline hydrochloride (5 parts) are uniformly admixed, and the resulting mixture is pressed to a sheet having a 500µ thickness.

EXPERIMENT 1

The controlled release of an active ingredient was evaluated on the pharmaceutical composition of the invention which contains two kinds of active ingredients.

METHOD AND MATERIALS (1) Preparation of Sample

Methacrylic acid / methyl methacrylate copolymer (1:2 molar ratio) (80 parts) was dissolved in ethanol (1000 parts). Triacetin (20 parts) and tetracycline hydrochloride (6 parts) were then mixed with the resultant solution. The mixture was casted on a Teflon tray and dried at 40° C. The resultant sheet was pulverized into particles of 105µ to 177µ in size.

On the other hand, hydroxypropyl cellulose (viscosity of 2% aqueous solution is 1000 to 4000 cp at 20° C.) (one part) was dissolved in water (99 parts). In the solution was dissolved tetracaine hydrochloride (0.03 part).

The hydroxypropyl cellulose solution and the particles are uniformly admixed at a weight ratio of 100:0.5, and the mixture is deaerated, casted on a Teflon tray with care to ensure the constant thickness, and air-dried to yield a film having 300µ thickness.

In a solution of hydroxypropyl cellulose (1 part) dissolved in water (100 parts) were dissolved tetracycline hydrochloride (0.02 part) and tetracaine hydrochloride (0.02 parts), and the mixture was adjusted to pH 6, deaerated, casted on a Teflon tray, air-dried to obtain a film having 300 thickness, which was employed as a reference.

(2) Evaluation of Dissolution Rate

The dissolution rates of the active ingredients released from the films obtained above were measured using a phosphate buffer (500ml), pH 7.2, at 37° C., in accordance with the Rotating Basket Method (100 rpm) of Japanese Pharmacopoeia (X).

RESULTS

Figure 2:
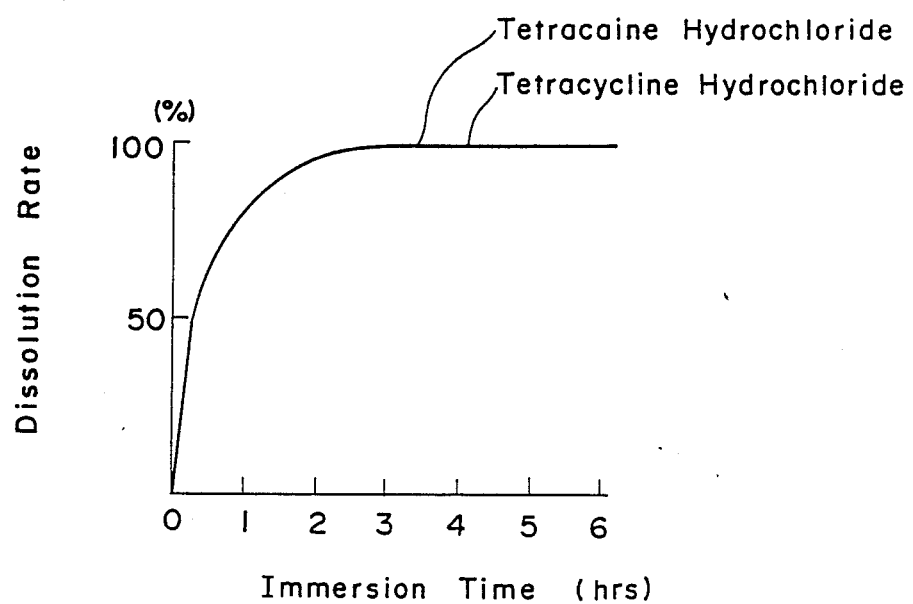
FIG. 2 shows the dissolution profile of two active ingredients contained in a conventional composition.

The dissolution profiles of the film of the invention and that of the reference are respectively shown in FIG. 1 and FIG. 2 of the accompanying drawing. The abscissa indicates immersion time and the ordinate indicates the dissolution rate. FIG. 1 shows that two active ingredients were released from the film with different release patterns while FIG. 2 shows the same and identical release pattern of the two active ingredients. Thus, this experiment illustrates that the composition of the invention permits separate control of the release patterns of two active ingredients. It also teaches that the composition of the invention in the form of a sustained release formulation may be obtained where the same and identical active ingredient rather than the two active ingredients is employed in this experiment.

What is claimed is:

1. A controlled-released pharmaceutical composition in the form of gel, sheet, film, or bar to be inserted or placed into a periodontal pocket for treating a periodontal disease, said composition comprising a therapeutically effective amount of at least one active agent effective for the treatment of the periodontal disease, said active agent being dispersed in a two-phase carrier consisting of
    (a) a continuous phase consisting of a watersoluble polymer capable of dissolving in water at a concentration of more than 1% by weight irrespective of pH, and
    (b) a discontinuous phase consisting of solid particles composed of a polymer capable of dissolving in water at a concentration of between about 0.1% and 1.0% by weight or solid particles composed of a polymer capable of dissolving in water having a pH higher than 4.0 or a pH lower than 6.0, at a concentration of more than 1% by weight,
said particles having an average size ranging from 1 $\mu$ to 500 $\mu$ and being dispersed in said water-soluble polymer, with the weight ratio of said particles to said water-soluble polymer ranging from 1:99 to 99:1 on a dry weight basis, said water-soluble polymer being selected from the group consisting of methyl cellulose, hydroxypropyl cellulose, sodium carboxymethyl cellulose, hydroxypropylmethyl cellulse, hydroxyethyl cellulose, sodium alginate, propylene glycol alginate, pullulan, tragacanth, xanthan gum, chitosan, polyethylene oxide, polyvinyl pyrrolidone, polyvinyl alcohol, polyacrylic acid, polymethacrylic acid, and salts thereof, and said solid particles being selected from the group consisting of poly(glycolic acid), poly(lactic acid), polytetramethylglycolide, polydiethylglycolide, polyϵ-caprolactone, poly(DL-decalactone), poly(alkyleneadipate), methylacrylate/methacrylic acid copolymer, methylacrylate/methacrylic acid/octylacrylate copolymer, ethyl acrylate/methacrylic acid copolymer, methylacrylate/ methacrylic acid/methylmethacrylate copolymer, methyl methacrylate/methacrylic acid copolymer, cellulose acetate phthalate, cellulose acetate succinate, cellulose acetate maleate, starch acetate phthalate, amylose acetate phthalate, methyl cellulose phthalate, hydroxypropylmethyl cellulose phthalate, hydroxyethyl ethylcellulose phthalate, hydroxypropylmethyl cellulose acetate succinate, carboxymethylethyl cellulose, polyvinylalcohol phthalate, polyvinyl acetate phthalate, polyvinylacetal phthalate, polyvinylbutylate phthalate, methylmethacrylate/dimethylaminoethyl methacrylate copolymer, and polyvinylacetal/dimethylamino acetate.

2. The composition of claim 1 wherein two active agents are dispersed in said carrier.

3. In the art of applying at least one active agent useful for the treatment of periodontal disease dispersed in a polymeric carrier directly to a periodontal pocket to thereby be released from the carrier at a controlled rate, the improvement consisting of the step of placing in the periodontal pocket a gel, bar, strip or film consisting of a therapeutically effective amount of the active ingredient dispersed in a two-phase carrier consisting of
    (a) a continuous phase consisting of a water-soluble polymer capable of dissolving in water at a concentration of more than 1% by weight irrespective of pH, and
    (b) a discontinuous phase consisting of solid particles composed of a polymer capable of dissolving in water at a concentration of between about 0.1% and 1.0% by weight or solid particles composed of a polymer capable of dissolving in water having a pH higher than 4.0 or a pH lower than 6.0, at a concentration of more than 1% by weight,
said articles having an average size ranging from 1 $\mu$ to 500 $\mu$, and being dispersed in said water-soluble polymer, with the weight ratio of said particles to said water soluble polymer ranging from 1:99 to 99:1 on a dry weight basis.

4. The method of claim 3 wherein two active agents are dispersed in said carrier.

* * * * *

UNITED STATES PATENT AND TRADEMARK OFFICE
CERTIFICATE OF CORRECTION

PATENT NO. : 4,933,182

DATED : June 12, 1990

INVENTOR(S) : Kiyotsugu Higashi et al

It is certified that error appears in the above-identified patent and that said Letters Patent is hereby corrected as shown below:

ON THE TITLE PAGE: Item [54] after the word "PERIODONTAL" insert the word --Diseases--.

Signed and Sealed this

Third Day of December, 1991

*Attest:*

HARRY F. MANBECK, JR.

*Attesting Officer*     *Commissioner of Patents and Trademarks*